US00PP36212P2

(12) United States Plant Patent
Ballington, Jr. et al.

(10) Patent No.: US PP36,212 P2
(45) Date of Patent: Oct. 22, 2024

(54) ***VACCINIUM* PLANT NAMED 'NC4499'**

(50) Latin Name: *Vaccinium corymbosum*
Varietal Denomination: NC4499

(71) Applicant: North Carolina State University, Raleigh, NC (US)

(72) Inventors: James Ralph Ballington, Jr., Cary, NC (US); Hudson Ashrafi, Cary, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 18/583,452

(22) Filed: Feb. 21, 2024

(51) Int. Cl.
*A01H 5/08* (2018.01)
*A01H 6/36* (2018.01)

(52) U.S. Cl.
USPC ..... Plt./157
CPC ..... *A01H 6/36* (2018.05)

(58) Field of Classification Search
USPC ..... Plt./157
CPC ..... A01H 5/08
See application file for complete search history.

*Primary Examiner* — Kent L Bell

(57) ABSTRACT

A new and distinct cultivar of *Vaccinium* plant named 'NC4499' is disclosed, characterized by attractive glaucous light blue-green foliage, and self-pollinating flowers developing into light blue fruit. Fruit is juicy and sweet. The new variety shows long-term survival under field conditions, and a heightened resistance to blueberry leaf rust. Plants are semi-evergreen in the Southeastern United States and maintain an attractive tidy shape long-term, including without pruning. Plants are suitable for pruning. The new variety is a *Vaccinium*, normally used as an ornamental garden or landscape plant.

3 Drawing Sheets

Latin name of the genus and species: *Vaccinium corymbosum.*

Variety denomination: 'NC4499'.

BACKGROUND OF THE INVENTION

The new cultivar was discovered as the product of a breeding program with the objective of breeding new varieties with abundant, edible fruits, attractive foliage color, and mounded habits. 'NC4499' was selected from the crossing of the seed parent, *Vaccinium* 'Sunshine Blue', unpatented, and the pollen parent, an unpatented, internally selected Vaccinium referred to by code 'NC3048'. The crossing resulting in the new variety was made in 1995 at a greenhouse in Raleigh, North Carolina.

'NC4499' was selected by the inventors as an interesting new variety in 2003, at a research greenhouse in Jackson Springs, North Carolina.

Asexual reproduction of the new cultivar 'NC4499' by softwood cuttings was performed at a greenhouse in Raleigh, North Carolina in 2003. Vegetative reproduction by cuttings has produced multiple generations and has shown that the unique features of this cultivar are stable and reproduced true to type through successive generations. Date of first sale was on Jun. 27, 2023, in the United States. This sale was made directly by the inventor or one who obtained the claimed invention directly or indirectly from the inventor. This sale and all public disclosures made between Jun. 27, 2023, and the filing of this application fall within the exception allowed under 102(b)(1).

SUMMARY OF THE INVENTION

The cultivar 'NC4499' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NC4499'. These characteristics in combination distinguish 'NC4499' as a new and distinct *Vaccinium* cultivar:

1. Attractive glaucous light blue-green foliage.
2. Foliage which is partially evergreen in the Southeastern US and fully evergreen in the Pacific Northwest.
3. Heightened resistance to blueberry leaf rust compared to other commercially available cultivars known to the inventor.
4. Long-term survival under field conditions.
5. Maintains an attractive, "tidy" shape long term even without pruning, but is amenable to pruning and shaping.
6. Self-pollinating flowers that develop into small to medium-sized light blue fruit.
7. Fruit which is juicy and sweet with excellent flavor.

PARENT COMPARISONS

Plants of the new cultivar 'NC4499' are similar to plants of the seed parent in most horticultural characteristics. However, plants of the new cultivar 'NC4499' differ in the following:

1. Plants of the new variety are less susceptible to blueberry leaf rust than plants of the seed parent.
2. Plants of the new variety exhibit an increased long-term survival under field conditions than plants of the seed parent.
3. Plants of the new variety maintain attractive/tidy plant appearance long term, even without pruning. Plants of the seed parent decline in attractiveness over time.

Plants of the new cultivar 'NC4499' are similar to plants of the pollen parent in most horticultural characteristics. However, plants of the new cultivar 'NC4499' differ in the following:

1. Plants of the new variety exhibit an increased long-term survival under field conditions than plants of the pollen parent.
2. Fruit of the new variety is larger than fruit of the pollen parent.
3. Fruit color of the new variety is a glaucous light blue, while the fruit color of the pollen parent is dark blue.
4. Ideal blooming period of the new variety ensures reliable annual fruit production. Early blooming period of the pollen parent often leads to loss of fruit due to frost.

COMMERCIAL COMPARISON

'NC4499' can be compared to the commercial variety *Vaccinium corymbosum* 'ZF06-043', U.S. Plant Pat. No. 23,325. Plants of the new variety are similar to 'ZF06-043' in most horticultural characteristics, however, 'NC4499' differs in the following:

1. Plants of the new variety are larger than plants of this comparator.
2. Leaves of the new variety are more narrowly elliptic, while leaves of this comparator are more broadly elliptic.
3. Foliage color of the new variety is more blue, while the foliage color of this comparator is more green.
4. Plants of the new variety are more loosely branched, while plants of this comparator are more densely branched.

BRIEF DESCRIPTION OF THE PHOTOGRAPHS

The accompanying photographs illustrate the following:

Figure 1:
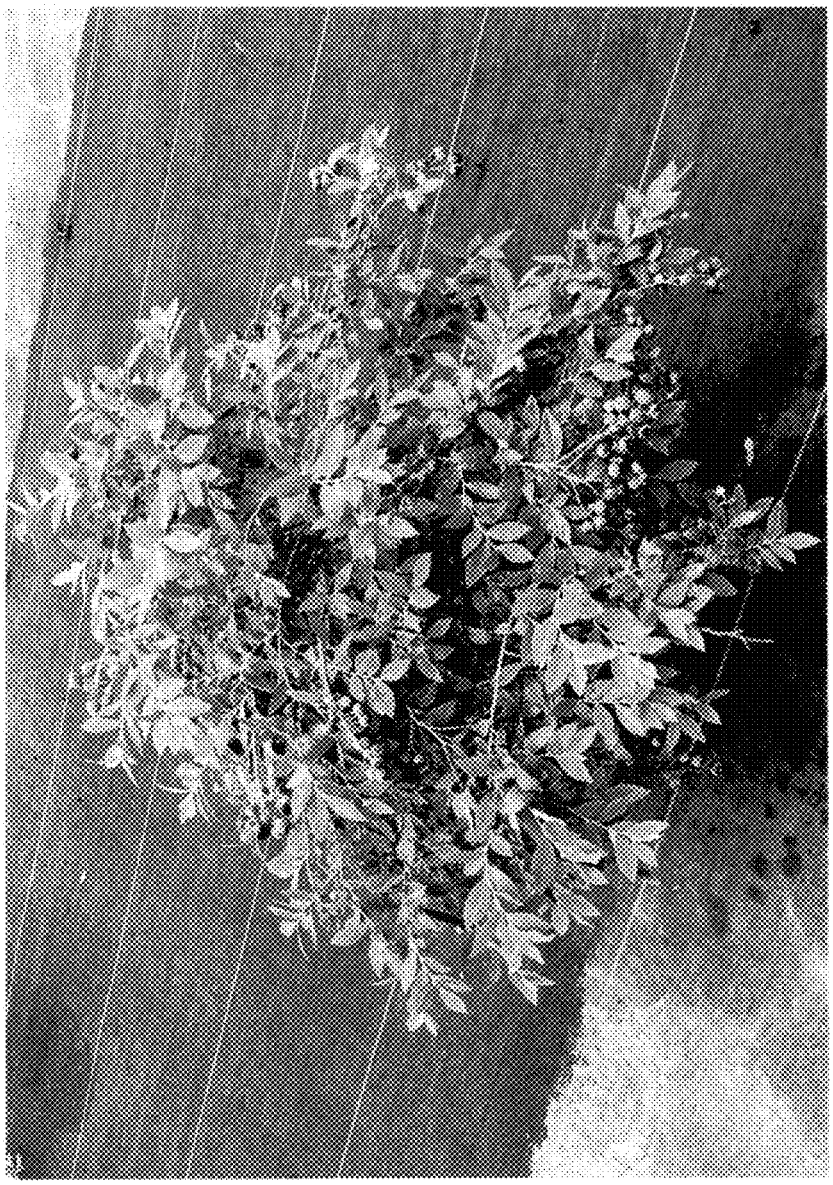
FIG. 1 illustrates in full color a typical plant of 'NC4499' in a 3-gallon pot grown outdoors in Grand Haven, MI. This plant is approximately 2 to 3 years old.
Figure 2:
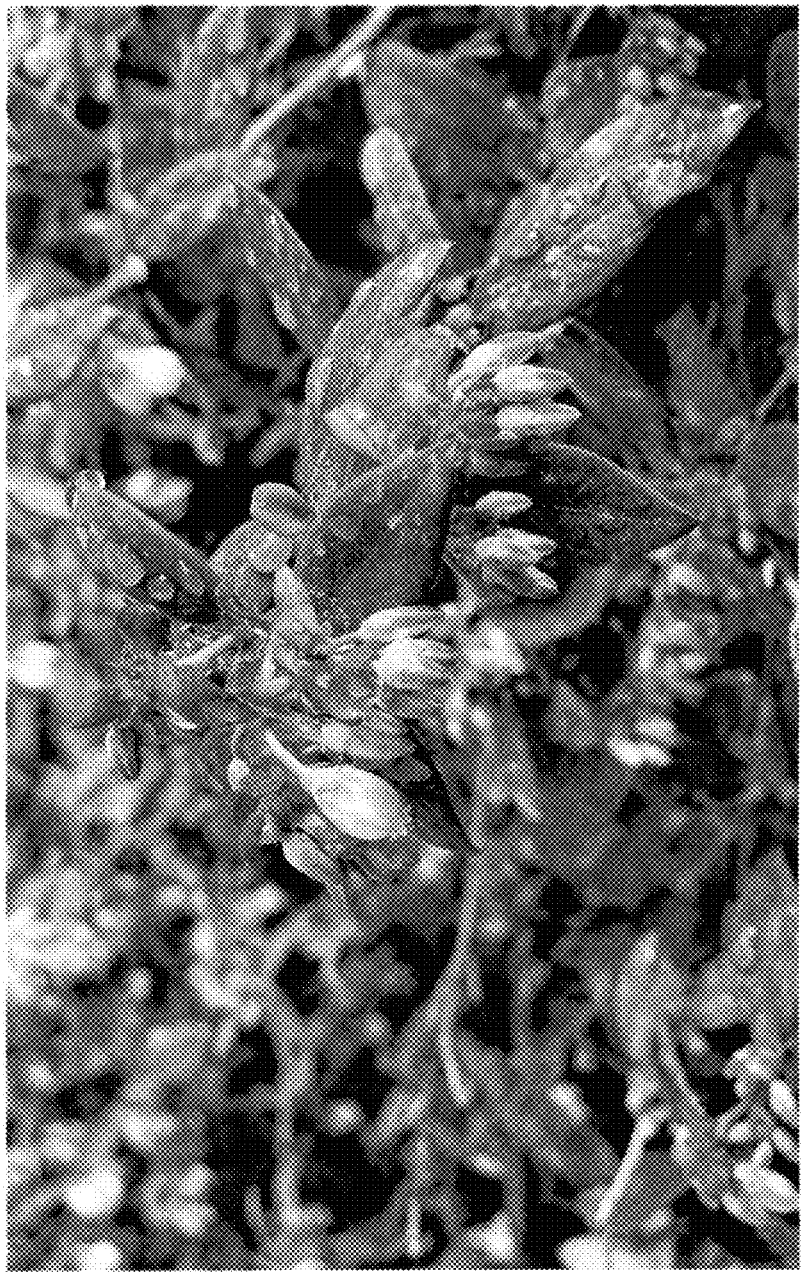
FIG. 2 illustrates in full color typical immature and mature flowers of 'NC4499'.
Figure 3:
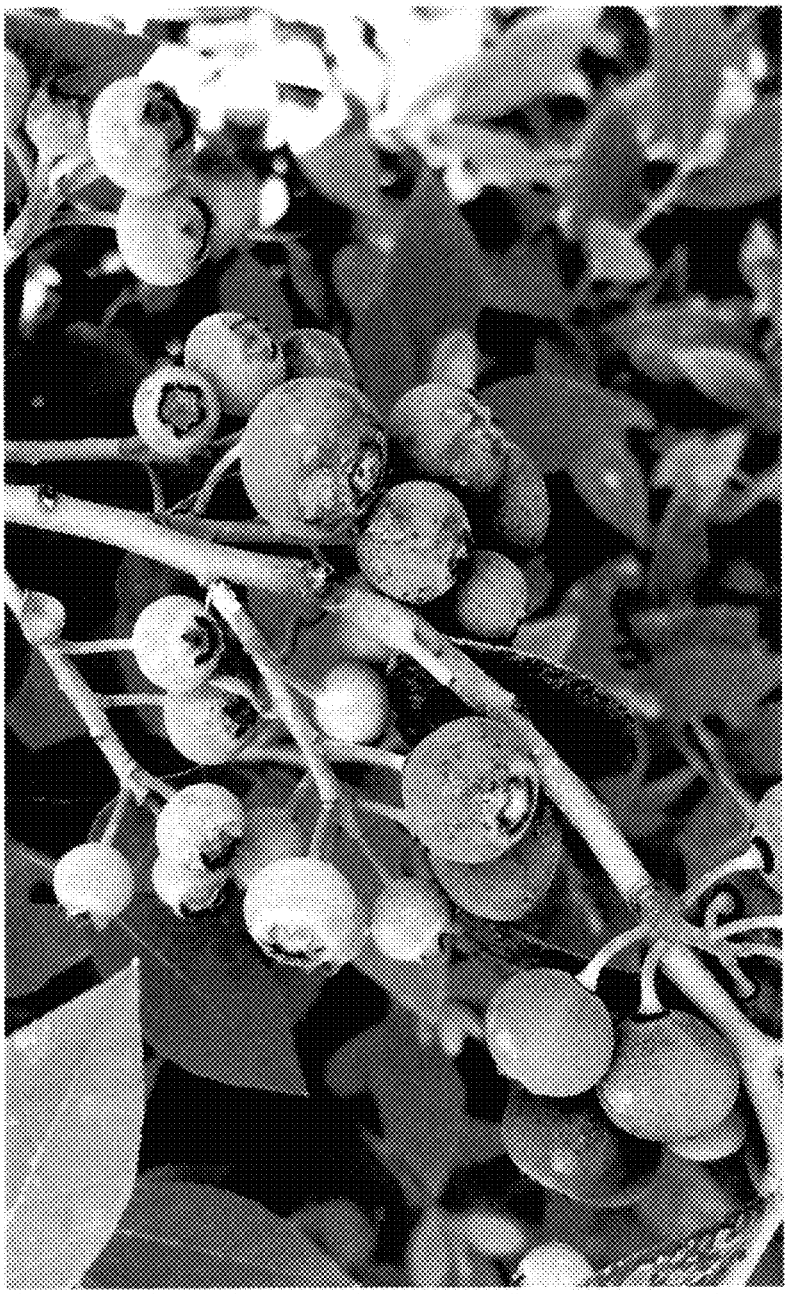
FIG. 3 illustrates in full color typical mature and immature fruit on a plant of 'NC4499'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'NC4499' plants grown outdoors in Grand Haven, Michigan. Year-round temperature ranged from approximately −12° to 32° C., day and night. Measurements and numerical values represent averages of typical flowering types. No chemical or photoperiodic treatments were given. Botanical classification: *Vaccinium corymbosum* 'NC4499'.

PROPAGATION

Method: Softwood cuttings.

Time to produce a rooted cutting: 42 days at 18° to 27° C. in summer.

Root description: Moderately dense, freely branching, thin, and fibrous. Tan to light brown in color, not accurately measured using R.H.S. Chart.

PLANT

Age of plant described: 2 to 3 years old, planted the ground.

Growth habit: Perennial shrub.

Height: Approximately 66 cm.

Plant spread: Approximately 80 cm.

Growth habit: Upwards and somewhat outwards.

Growth rate: Good.

Vigor: Fairly vigorous.

Branching habit: Basal; some pinching required.

Lateral branches:

*Quantity.*—10 to 15.
*Length.*—30 to 50 cm.
*Diameter.*—5 mm.
*Shape.*—Rounded.
*Pubescence.*—None.
*Color.*—New growth: R.H.S. Yellow-Green N144A with a slight tint of Greyed-Red 178A on the upper side. Old growth: R.H.S. Brown N200C.
*Aspect.*—45° to 75°.
*Strength.*—Strong.

Internode length: 1 cm.

FOLIAGE

Leaf:

*Arrangement.*—Alternate, single.
*Length.*—Approximately 2 cm.
*Width.*—Approximately 7.6 cm.
*Shape.*—Elliptic to narrowly elliptic.
*Apex.*—Acute.
*Base.*—Cuneate.
*Margin.*—Entire.
*Texture of top surface.*—Glabrous.
*Texture of bottom surface.*—Glabrous.
*Pubescence.*—None.
*Color.*—Young foliage upper side: R.H.S. Green 137B. Young foliage under side: R.H.S. Green 138B to 138C. Mature foliage upper side: R.H.S. Green 137B. Mature foliage under side: R.H.S. Green 138B to 138C.
*Venation.*—Type: Pinnate. Venation color upper side: R.H.S. Green 138B to 138C. Venation color under side: R.H.S. Green 138B to 138C.
*Petiole.*—Length: 1 mm. Diameter: 1 mm. Texture: Both sides glabrous. Color upper side: R.H.S. Yellow-Green 145B. Color under side: R.H.S. Green 145B.

FLOWER

Natural flowering season: June.

Flower type and habit: Urceolate, flowering terminally and axillary.

Quantity of flowers: 200 to 300 per lateral stem.

Quantity of buds: 50 to 100 per lateral stem.

Quantity of flowers and buds: Thousands per plant.
Fragrance: None.
Bud:
*Shape*.—Oblong.
*Length*.—6 mm.
*Diameter*.—3 mm.
*Color*.—R.H.S. Greyed-Red 181A to 181B adaxially, fading to Yellow-Green 145C abaxially.
Flower:
*Shape*.—Urecolate.
*Diameter*.—6 mm.
*Length*.—1 cm.
*Depth*.—1 cm.
*Aspect*.—Drooping.
*Persistence*.—Self-cleaning.
Petals:
*Quantity*.—5.
*Arrangement*.—Whorl.
*Length*.—8 mm.
*Width*.—3 mm.
*Appearance*.—Fused into a bell shape, terminating in a stellate whorl of diminutive, triangular, outwardly furled petals.
*Shape*.—Triangular.
*Apex*.—Acute.
*Base*.—Fused.
*Margin*.—Entire.
*Texture, upper and lower surfaces*.—Glabrous, silky.
*Color*.—When opening, upper side: R.H.S. Yellow-Green 145C with an irregular Greyed-Red 181D blush. When opening, under side: R.H.S. Yellow-Green 145C. Fully opened, upper side: R.H.S. Green-White 157D with an irregular Greyed-Red 181D blush. Fully opened, under side: R.H.S. Green-White 157D.
Sepals:
*Quantity*.—5.
*Arrangement*.—Whorl.
*Length*.—3 mm.
*Width*.—2 mm.
*Appearance*.—Small, pointed, cupping.
*Shape*.—Ovoid.
*Apex*.—Acute.
*Base*.—Fused.
*Margin*.—Entire.
*Texture, upper and lower surfaces*.—Glabrous.
*Color*.—Mature, upper side: R.H.S. Yellow-Green 144A. Mature, under side: R.H.S. Yellow-Green 144A.
Calyx:
*Length*.—4 mm.
*Width*.—6 mm.
*Shape*.—Collar-like stellate whorl, becoming fused at the base.
Peduncles:
*Length*.—9 mm.
*Diameter*.—1 mm.
*Strength*.—Good, somewhat flexible.
*Angle*.—45°.
*Texture*.—Glabrous.
*Color*.—R.H.S. Yellow-Green 144B.

REPRODUCTIVE ORGANS

Stamens:
*Number*.—Typically 10.
*Filament color*.—R.H.S. Green-White 157D.
*Filament length*.—2 mm.
Anthers:
*Shape*.—Long, spur like thecae which are fused at the bottom third and the remainder are separate.
*Length*.—4 mm.
*Color*.—R.H.S. Greyed-orange 166B at base, becoming Greyed-orange 167B towards tip.
*Pollen amount*.—Sparse.
Pistil:
*Number*.—1.
*Length*.—1 cm.
*Style*.—Length: 1 cm. Color: R.H.S. Yellow-Green 144B.
*Stigma*.—Shape: Rounded. Color: R.H.S. Yellow-Green 144B. Ovary Color: R.H.S. Yellow-Green 147A.

FRUIT AND SEEDS

Fruit:
*Quantity*.—30 to 50 per lateral branch; 400 to 700 per About 5 to 7 per cluster.
*Color*.—Immature: Upper side: R.H.S. Orange-Red 35A. Under side: R.H.S. Yellow-Green N144D. Fully ripe: On plant: Closest to R.H.S. Black 202B bloom over Black 202A. Polished off bloom: R.H.S. Black 202A.
*Length*.—1 cm.
*Diameter*.—1 cm.
*Texture*.—Smooth-skinned fruit that is juicy on the inside with a small number of small, crunchy seeds.
*Taste*.—Berry is quite sweet but with a definite fruity taste and tartness; balanced.
*Firmness*.—Firm.
*Flesh color*.—About 145C.
*Stem length*.—About 1 cm.
Seeds:
*Quantity*.—Around 2 per fruit.
*Length*.—1 mm.
*Diameter*.—0.5 mm.
*Color*.—R.H.S. Greyed-Orange 167A.

OTHER CHARACTERISTICS

Disease resistance: Increased resistance to blueberry leaf rust.
Pest resistance: Neither resistance nor susceptibility to the normal pests of *Vaccinium*.
Environmental tolerance: Excellent tolerance to rain and wind.
Hardiness: USDA Hardiness Zones 6A to 9.

What is claimed is:

1. A new and distinct cultivar of *Vaccinium* plant named 'NC4499' as herein illustrated and described.

* * * * *